US00PP24006P2

(12) United States Plant Patent
Hanes

(10) Patent No.: US PP24,006 P2
(45) Date of Patent: Oct. 29, 2013

(54) ***VERBENA* PLANT NAMED 'VEAZ0011'**

(50) Latin Name: *Verbena×hybrida*
Varietal Denomination: VEAZ0011

(75) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 167 days.

(21) Appl. No.: 13/373,034

(22) Filed: Nov. 2, 2011

(51) Int. Cl.
*A01H 5/00* (2006.01)

(52) U.S. Cl.
USPC ..... Plt./308

(58) Field of Classification Search
USPC ..... Plt./308
See application file for complete search history.

(56) References Cited

PUBLICATIONS

PLUTO: Plant Variety Database, citation for *Verbena* plant named 'VEAZ0011' (CA PBR 11-7314, filed Jun. 10, 2011) https://www3.wipo.int/pluto/user/en/index.jsp.*

PLUTO: Plant Variety Database, citation for *Verbena* plant named 'VEAZ0011' (QZ PBR 20111599, filed Jun. 27, 2011) https://www3.wipo.int/pluto/user/en/index.jsp.*

* cited by examiner

*Primary Examiner* — Howard Locker
(74) *Attorney, Agent, or Firm* — Joshua L. Price

(57) ABSTRACT

A new *Verbena* plant named 'VEAZ0011' particularly distinguished by the red and white bi-colored flowers, medium-dark yellow-green foliage, good branching and vigor, with a semi-trailing habit.

1 Drawing Sheet

Latin name of the genus and species of the plant claimed: *Verbena×hybrida.*

Varietal denomination: 'VEAZ0011'.

BACKGROUND OF THE NEW PLANT

The present invention comprises a new *Verbena*, botanically known as *Verbena×hybrida*, and hereinafter referred to by the variety name 'VEAZ0011'.

'VEAZ0011' is a product of a planned breeding program. The new cultivar has red and white bi-colored flowers, medium-dark yellow-green foliage, good branching and vigor, with a semi-trailing habit.

'VEAZ0011' originated as a naturally occurring branch mutation in August 2008 on a plant growing in a field trial in Gilroy, Calif. The mutation was found on the proprietary plant designated 'Lan Reda07', U.S. Plant Pat. No. 18,986, with solid red flower color.

The first act of asexual reproduction of 'VEAZ0011' was accomplished when vegetative cuttings were propagated from the initial mutation selection in August 2008 in a controlled environment in Gilroy, Calif.

BRIEF SUMMARY OF INVENTION

Horticultural examination of plants grown from cuttings of the plant initiated in August 2008, and continuing thereafter, has demonstrated that the combination of characteristics as herein disclosed for 'VEAZ0011' are firmly fixed and are retained through successive generations of asexual reproduction.

'VEAZ0011' has not been observed under all possible environmental conditions. The phenotype may vary significantly with variations in environment such as temperature, light intensity and day length.

Plant Breeder's Rights for this cultivar were applied for in Canada on Jun. 10, 2011, #10-7314 and in the Community Plant Variety Office on Jun. 27, 2011, #2011/1599. 'VEAZ0011' has not been made publicly available more than one year prior to the filing of this application.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawing shows typical flower and foliage characteristics of 'VEAZ0011' with colors being as true as possible with an illustration of this type.

Figure 1:
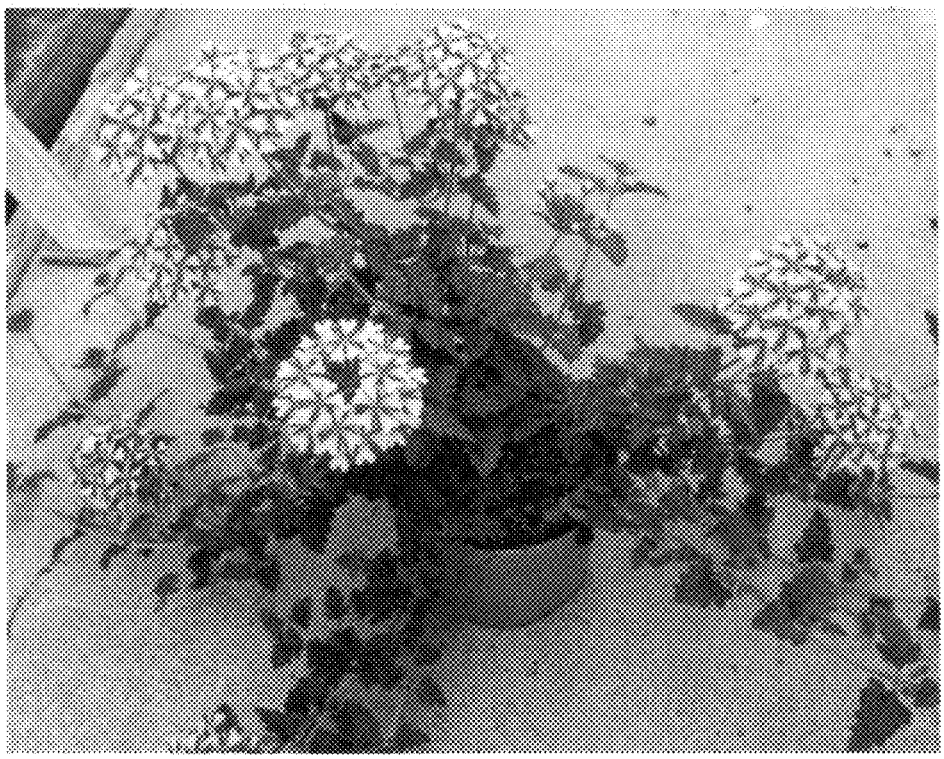
Figure 2:
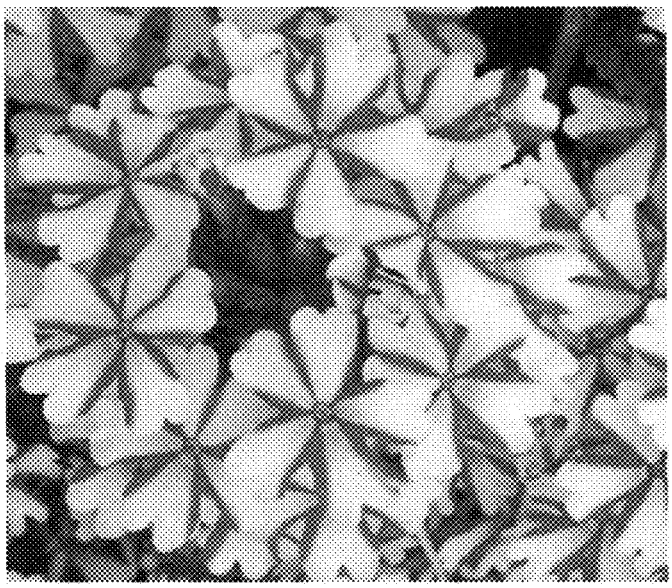

The photographic drawing shows in FIG. 1. a flowering plant of the new variety, and in FIG. 2. a close-up of the flowers.

DETAILED BOTANICAL DESCRIPTION

The aforementioned photographs were taken in April 2011 from plants growing in a greenhouse trial in Andijk, Netherlands. These plants were growing in 10 cm pots and were approximately 9-11 weeks of age.

The plant descriptions and measurements were taken in July 2011 in Gilroy, Calif. from plants grown in a outdoor basket trial on about 16 week old plants.

Color references are made to The Royal Horticultural Society Colour Chart (R.H.S.) 2001.

TABLE 1

DIFFERENCES BETWEEN THE NEW VARIETY 'VEAZ0011' AND A SIMILAR VARIETY

| | 'VEAZ0011' | 'Estrella Voodoo Star' (Unpatented) |
|---|---|---|
| Flower color pattern: | White with red margins | Red with white margins |
| Vigor: | More vigorous | Less vigorous |
| Flower size: | Smaller | Larger |

Plant:

*Form, growth and habit.*—Herbaceous, initially spreading, later becoming decumbent to trailing.

*Plant height.*—7.0-8.0 cm.

*Plant height (inflorescence included).*—10.0-12.0 cm.

*Plant width.*—About 35.0 cm.

Roots:

*Number of days to initiate and produce roots.*—About 10-14 days at about 22 degrees C.

*Type.*—Fine, fibrous, free branching.

*Color.*—RHS N155B.

Foliage:

*Arrangement.*—Opposite, simple.

*Immature, leaf color, upper surface.*—Closest to RHS 147A.

*Lower surface.*—Closest to RHS 137C.

*Mature, leaf color, upper surface.*—Closest to RHS 147A.

*Lower surface.*—Closest to RHS 137C.

*Length.*—2.8-3.0 cm.

*Width.*—2.2-2.4 cm.

*Shape.*—Ovate.

*Base shape.*—Attenuate.

*Apex shape.*—Acute.

*Margin.*—Irregularly serrate.

*Texture, upper surface.*—Pilose.

*Lower surface.*—Pilose, few glandular hairs mostly on the mid-veins.

*Color of veins, upper surface.*—RHS 144C.

*Color of veins, lower surface.*—RHS 144C.

*Petiole color.*—RHS 144C.

*Length.*—0.4-0.5 cm.

*Diameter.*—0.2 cm.

*Texture.*—Heavily pilose.

Stem:

*Number of main stems per plant.*—8-10.

*Color of stem.*—RHS 138A but a little greener.

*Length of stem.*—About 30.0 cm.

*Diameter.*—0.3 cm.

*Length of internodes.*—2.0-4.0 cm.

*Texture.*—Pilose, hirtellous, glandular hairs.

*Color of peduncle.*—RHS 144A but a little lighter.

*Length of peduncle.*—5.5-9.0 cm.

*Peduncle diameter.*—0.15-0.2 cm.

*Texture.*—Pilose, glandular hairs.

Inflorescence:

*Type.*—Umbel-like, but actually a spike, umbrella-shaped to roughly semi-spherical.

*Blooming habit.*—Flowers continuously.

*Quantity of inflorescences per plant.*—About 50.

*Lastingness of individual blooms on the plant.*—About 6 days in the greenhouse.

*Fragrance.*—None.

*Inflorescence horizontal diameter.*—5.2-5.5 cm.

*Inflorescence depth (height).*—2.7-3.5 cm.

*Quantity of flowers and buds per inflorescence.*—10-15.

Bud (just when starting to show color):

*Color.*—RHS 67A with RHS 63D basally.

*Length.*—1.3-1.5 cm.

*Width.*—0.3-0.4 cm.

*Shape.*—Tubular with bulbous end.

Floret:

*Form and type.*—Sessile; salverform, composed of 5 partly fused petals with a base of a narrow tube.

*Immature color, upper surface.*—RHS 155B, with a hue of lighter than RHS N57A basally around the throat, and RHS 46A to RHS 46B at the inner margins.

*Lower surface.*—RHS 155B with RHS 46B inner margins.

*Mature color, upper surface.*—RHS 155B, with a hue of lighter than RHS N57A basally around the throat, and RHS 46A to RHS 46B at the inner margin.

*Lower surface.*—RHS 155B with RHS 46B inner margins.

*Floret diameter.*—About 1.8 cm.

*Floret depth.*—About 2.0 cm.

All petals:

*Length of petals.*—0.7-0.9 cm.

*Width of petals.*—0.6-0.8 cm.

*Petal shape.*—Obovate.

*Apex shape.*—Retuse.

*Margin.*—Entire.

*Petal texture, upper surface.*—Papillose.

*Lower surface.*—Papillose.

*Corolla tube color inside.*—RHS 1C to RHS 1D and more translucent; with throat hairs of RHS N74D at the corolla opening.

*Tube color outside.*—RHS 1D.

*Corolla tube length.*—2.0-2.3 cm.

*Corolla texture, inside.*—Papillose; with hairs at the corolla flare (throat).

*Outside.*—Papillose.

Calyx:

*Type.*—Five sepals whose margins are fused to each other along their length, with a transparent membrane of less than 0.1 cm in width and with one smaller sepal attached to the base of the calyx.

*Color of sepals.*—RHS 138A to RHS 138B.

*Length of sepals.*—1.0-1.2 cm.

*Width of sepals.*—0.2-0.25 cm.

*Sepal shape.*—Linear.

*Apex shape.*—Acute.

*Margins.*—Entire, but fused mostly.

*Texture, upper surface.*—Glabrous.

*Lower surface.*—Pilose, glandular hairs.

Reproductive organs:

*Pistil.*—1.

*Length.*—About 1.8 cm.

*Style color.*—RHS 1C.

*Style length.*—1.5 cm.

*Stigma color.*—RHS 147C.

*Ovary color.*—RHS 146D.

*Ovary length.*—0.15 cm.

*Ovary width.*—0.1 cm.

*Stamens.*—4, anthers and filaments fused to upper half of corolla tube; anthers with two pollen sacs per anther.

*Color of filaments.*—RHS 149D with slight hint of about RHS 48B under the anthers.

*Length filaments.*—0.1-0.2 cm.

*Anther color.*—Between RHS 149C and RHS 149D.

*Length of anthers.*—0.1 cm.

*Color of pollen.*—RHS 149C.

*Pollen amount.*—Good.

*Fertility/seed set.*—Has not been determined to date.

*Disease/pest resistance.*—Has not been determined to date.

What is claimed is:

1. A new and distinct variety of *Verbena* plant named 'VEAZ0011' substantially as illustrated and described herein.

* * * * *